United States Patent [19]

Takahashi

[11] 4,110,047
[45] Aug. 29, 1978

[54] INSPECTION APPARATUS FOR AUTOMATICALLY DETECTING THE UNEVENNESS OR THE FLAWS OF A COATING

[75] Inventor: Tokuji Takahashi, Hino, Japan

[73] Assignee: Konishiroku Photo Industry Co., Ltd., Tokyo, Japan

[21] Appl. No.: 667,966

[22] Filed: Mar. 17, 1976

[30] Foreign Application Priority Data

Mar. 18, 1975 [JP] Japan .................................. 50-33322

[51] Int. Cl.$^2$ ............................................. G01N 21/32
[52] U.S. Cl. .................................... 356/200; 250/572; 356/237
[58] Field of Search .......................... 350/6, 7, 6.7, 6.8; 356/199, 200, 237; 250/571, 572

[56] References Cited

U.S. PATENT DOCUMENTS

| | | | |
|---|---|---|---|
| B 469,036 | 3/1976 | Neale et al. ................................ | 350/7 |
| 3,573,849 | 4/1971 | Herriot ....................................... | 350/7 |
| 3,825,351 | 7/1974 | Seki et al. ............................... | 356/237 |
| 3,841,761 | 10/1974 | Selgin ..................................... | 250/572 |
| 3,944,369 | 3/1976 | Cuthbert ................................. | 356/168 |

*Primary Examiner*—John K. Corbin
*Assistant Examiner*—R. A. Rosenberger
*Attorney, Agent, or Firm*—James E. Nilles

[57] ABSTRACT

A scanning inspection apparatus comprising two light beams each having a different angle of incidence to the surface of the object and light detecting means for receiving lights reflected by the surface of the object. Said two light beams are provided by a light beam generating means, a rotating mirror and a semitransparent mirror.

A plane including a light path of the light beam radiated by the light beam generating means and a light path of the light beam reflected by the rotating mirror is arranged to be perpendicular to the reflecting face of the rotating mirror.

10 Claims, 12 Drawing Figures

INSPECTION APPARATUS FOR AUTOMATICALLY DETECTING THE UNEVENNESS OR THE FLAWS OF A COATING

The present invention relates to an inspection apparatus for detecting irregularity on a surface of a plate, film and so forth, which irregularity includes, for examples, projection and hollow on the surface. This invention particularly relates to an inspection apparatus for detecting surface irregularity of a coating applied to photographic films and magnetic tapes. More particularly, this invention relates to an inspection apparatus capable of automatically and continuously detecting the irregularity of the coating during the manufacture of the film and the tape. It is required that the film and the tape should have a surface or surfaces of a coating or coatings which has even and regular surface. However, there can not be avoided such a possibility that the coating has surface irregularities such as projections, dents and hollows as shown in FIGS. 1b, 1c and 1d with numerals 3, 4 and 5.

Heretofore, there have been provided various inspection apparatuses for detecting the irregularity.

However, conventional apparatus was unsatisfactory in detection sensitivity and has various drawbacks.

Accordingly, an object of the present invention is to provide an inspection apparatus free from the above mentioned drawbacks.

According to a first embodiment the present invention, the above mentioned object is accomplished by an inspection apparatus comprising a means for supporting and moving an object to be scanned; a light beam generating means; a rotating mirror for directing a light beam radiated by the light beam generating means to the object; a semitransparent mirror for dividing a light beam reflected by the rotating mirror into two light beams; plural mirrors for reflecting each of said two light beams divided by the semitransparent mirror through respective light paths having a length substantially same as each other to a point on the surface of the object; and light detecting means for receiving lights reflected by the surface of the object; wherein a plane including a light path of the light beam radiated by the light beam generating means and a light path of the light beam reflected by the rotating mirror is arranged to be perpendicular to the reflecting face of the rotating mirror.

According to an embodiment of the present invention, there is provided a second embodiment inspection apparatus in which two light beam generating means are provided for providing the two light beams in place of said one light beam generating means and two rotating mirrors for reflecting said two light beams.

According to a third another embodiment of the present invention, there is provided an inspection apparatus in which two light beam generating means are provided for providing the two light beams in place of said one light beam generating means and a rotating mirror for reflecting both of said two light beams.

These and other objects as well as merits of the present invention will be apparent from the following detailed description with reference to the accompanying drawings.

Firstly, there will be described the principle of the present invention.

Figure 1:
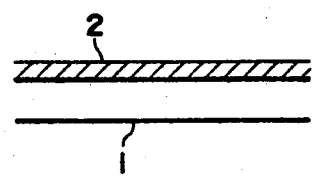
FIG. 1a is a section of a film having an emulsion layer uniformly coated on the base surface thereof.
FIG. 1b is a section of a film having an emulsion layer which has a projection.
FIG. 1c is a section of a film having an emulsion layer which has a dent.
FIG. 1d is a section of a film having an emulsion layer which has a hollow.
Figure 1:
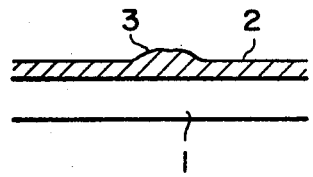
Figure 1:
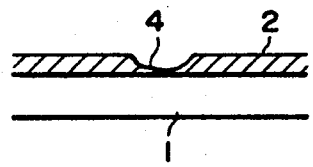
Figure 1:
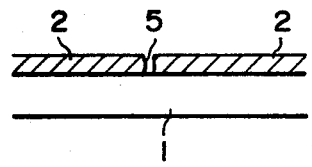

Such surface irregularities as shown in FIGS. 1b and 1c, that is, the irregularities formed at surface end is detected with high sensitivity by a light beam having a relatively large incident angle, but such surface irregularity shown in FIG. 1d, that is, irregularity of which depth is large to such an extent that the film base is naked can hardly be detected by a light beam having a relatively large incident angle.

The surface irregularity shown in FIG. 1d is detected with high sensitivity by a light beam having a relatively small incident angle.

The above mentioned facts will be explained below with reference to FIGS. 2a, 2b, 3a and 3b.

Figure 2:
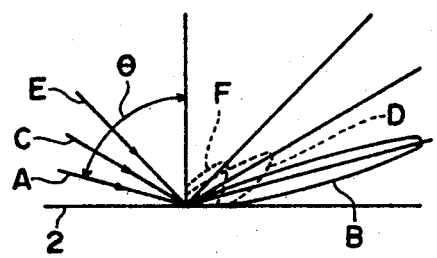
FIG. 2a is a diagram showing the scattering angular distribution function curve of the light beams reflected by the surface of a layer uniformly coated.
FIG. 2b is a diagram showing the scattering angular distribution function curve of the light beams reflected by the base surface of the film.
Figure 2:
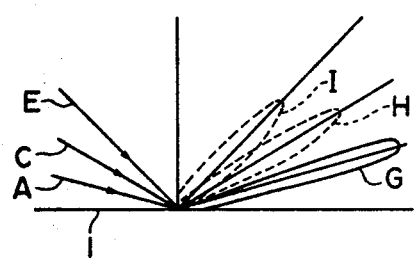

When parallel light beams consisting of laser beams or the like are radiated, changing their angles of incidence in various ways, to an emulsion layer 2 uniformly coated on a surface of the film base 1, there can be found such scattering angular distribution as shown in FIG. 2a. Namely, in case the angle $\theta$ of incidence of a light beam A is 75°, the scattering angular distribution in reflection is shown by a symbol B having a substantial regular reflection component, that of a light beam C, of which angle of incidence is 60°, is shown by a symbol D and that of a light beam E, of which angle of incidence is 45°, is shown by a symbol F having little regular reflection component.

On the other hand, in case the angles of incidence of the light beams radiated to the surface of the film base 1 are changed, the scattering angular distribution of the respective light beams are as shown in FIG. 2b. Namely, the scattering angular distribution of the light beam A, of which angle of incidence is 75°, is shown by a symbol G, that of the light beam C, of which angle of incidence is 60°, is shown by a symbol H and that of the light beam E, of which angle of incidence is 45°, is shown by a symbol I. It will be therefore seen that in case the light beams are radiated to the surface of the film base 1 all of these scattering angular distribution have a great regular reflection component and are relatively smaller in their angle difference compared with those of the light beams radiated to the emulsion layer 2. To add further, when the angle $\theta$ of incidence of the light beams is made smaller than 30°, there can be found a change in their respective regular reflection light reflected by the surface of the film base 1.

Figure 3:
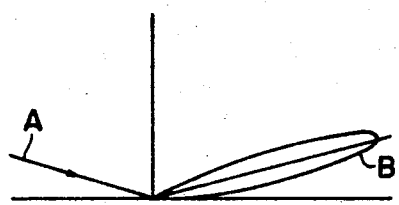
FIG. 3a is a diagram explaining how to detect such defects of the emulsion layer as shown in FIGS. 1b and 1c.
FIG. 3b is a diagram explaining how to detect such defect of the emulsion layer as shown in FIG. 1d.
Figure 3:
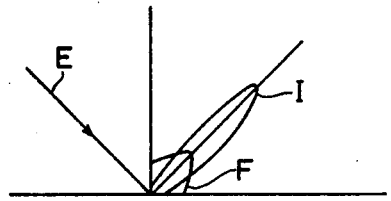

As apparent from the above, for the purpose of detecting such defects on the emulsion layer as shown in FIGS. 1b and 1c, it is desirable that the angle of incidence of the light beams is made larger so as to increase the regular reflection factor of the light beams reflected by the emulsion layer as shown in FIG. 3a.

As a result of tests it has been found that the angle of incidence of the light beams is preferably kept to be larger than 70°, more preferably about 75°.

In case emulsion is coated on the base surface of the film to have a portion at which emulsion is missed as shown in FIG. 1d, detection of this portion can be attained by the reflected light I from the surface of the film base 1, while selecting the angle of incidence of the light beam to be smaller than 45° so as to make the reflected light from the emulsion layer 2 as a diffused light F as shown in FIG. 3b.

In this case it has been found preferable from tests that the angle of incidence of the light beam is arranged to be smaller than 45°, more preferably about 30°.

Figure 4:
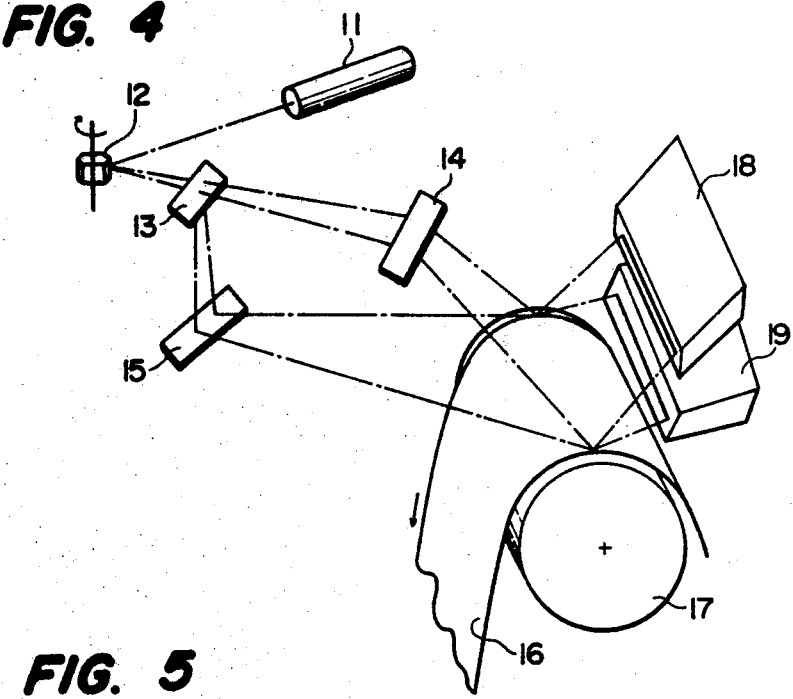
FIG. 4 is a perspective view showing an embodiment of the present invention.
Figure 5:
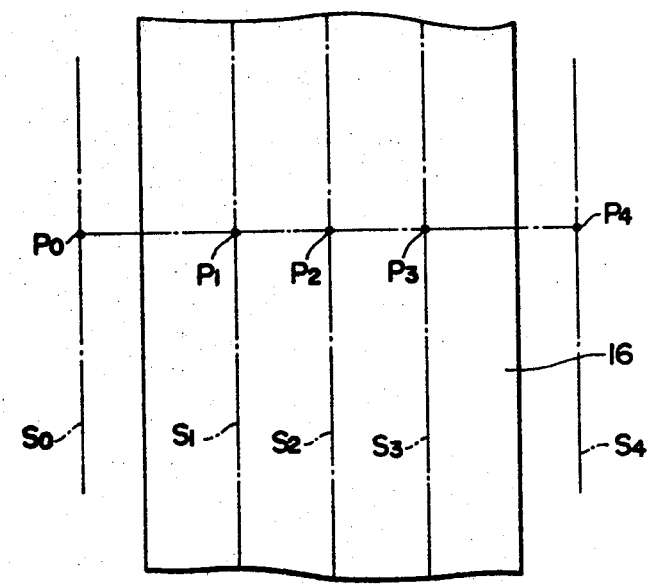
FIG. 5 is a diagram showing the relation between the scanning locus of the light beam and the object to be inspected.

In FIG. 4 numeral 11 represents a light beam generating means such as laser oscillator which is arranged to radiate a light beam perpendicular to the rotating shaft of a polygonal rotating mirror 12. The rotating mirror 12 is intended to direct the light beam from the light beam generating means 11 to an object 16 to be inspected and the rotating shaft of the mirror 12 is arranged to be perpendicular to the rotating shaft of a roller 17 which supports the object 16. Numeral 13 denotes a semitransparent mirror for dividing the light beam into two parts, the longitudinal axis of said semitransparent mirror 13 being arranged to be perpendicular to the rotating shaft of the mirror 12 and parallel to the rotating shaft of the roller 17. Numeral 14 represents a mirror for reflecting the light beam passed through the semitransparent mirror 13 so as to let the reflected light beam function as a scanning light to scan the surface of the object 16, the longitudinal axis of said mirror 14 being arranged to be parallel to the rotating shaft of the roller 17. Namely, the light beam generating means 11, the rotating mirror 12 and the mirror 14 are arranged on a common plane, and a plane including the light beam radiated by the light beam generating means 11 and the light reflected by the mirror 12 is arranged to be vertical to the face of the rotating mirror 12. Numeral 15 denotes another mirror for reflecting the light reflected by the semitransparent mirror 13 so as to let this reflected light function as another scanning light to scan the object 16 at an angle of incidence different from that of the scanning light from the mirror 14, the longitudinal axis of said mirror 15 being arranged to be parallel to the rotating shaft of the roller 17 and located at such a position as allows the scanning light spot from the mirror 15 to be overlapped on the surface of the object with the one from the mirror 14. Numeral 18 represents a light detecting means for receiving the light coming from the mirror 14 and being reflected by the surface of the object 16. Numeral 19 denotes another light detecting means for receiving the light coming from the other mirror 15 and being reflected by the surface of the object 16.

The inspection apparatus of the present invention, thus constructed, enables the whole surface of the object 16, being moved by the rotating roller 17, to be linearly scanned by the light beams under the condition that the scanning light spot from the mirror 14 is being overlapped with the one from the mirror 15.

Further, when the rotation of the rotating mirror 12 is arranged to be much faster than the moving speed of the object 16, the scanning locus of the scanning lights which are overlapped with each other on the surface of the object 16 will form a straight line running across the surface of the object 16. There is provided a device for detecting pulses from the light detecting means 18 and 19. This device is well known and therefore not shown. And this device is so constructed that a reference pulse signal is generated at each instant when the light spot on the surface of the object 16 reaches marginal lines $S_0$ and $S_4$, and intermediate lines $S_1$, $S_2$ and $S_3$, that is, at points $P_0$, $P_1$, $P_2$, $P_3$ and $P_4$ and recorded together with outputs from the light detecting means 18 and 19, the position of the surface irregularity of the film will be easily detected. One of advantages of the present invention exists in that a plane including a light path of the light beam radiated from the light beam generating means and a light path of the light beam reflected by the rotating mirror is so arranged to be perpendicular to the reflecting surface of the rotating mirror, whereby the scanning locus becomes linear and therefore the construction of the detecting means is made simple, and the accuracy of the detection is increased.

The greater the rotation speed is, the more accurate the determination of the position of the surface irregularity will be made.

Furthermore, the angle of incidence of each scanning light to the surface of the object can be varied according to the kind of defects present in the coating applied to the surface of the film by changing in various ways the position of each of the mirrors 14 and 15 in a range within which both of the scanning lights are kept equal or approximately equal in the length of their light paths.

Figure 6:
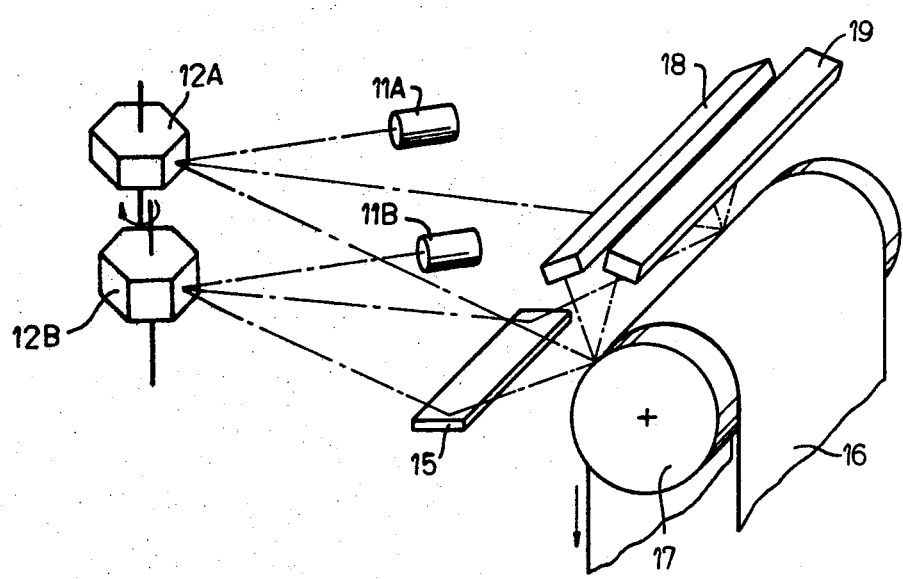
FIG. 6 is a view simlar to FIG. 4 showing a second embodiment of the invention.

In FIG. 6 numerals 11A and 11B represent a light beam generating means such as laser oscillators which are arranged to radiate two light beams perpendicular to the rotating shaft of polygonal rotating mirrors 12A and 12B, respectively. The rotating mirrors 12A and 12B are intended to direct the light beams from the light beam generating means 11A and 11B to the object 16 to be inspected and the rotating shafts of the mirrors 12A and 12B are arranged to be perpendicular to the rotating shaft of the roller 17 which supports the object 16. The reflected light beam from means 11A functions as a scanning light to scan the surface of the object 16. The light beam generating means 11A and the rotating mirror 12A are arranged on a common plane, and a plane including the light beam radiated by the light beam generating means 11A and the light reflected by the mirror 12A is arranged to be vertical to the face of the rotating mirror 12. Numeral 15 denotes another mirror for reflecting the light reflected by the rotating mirror 12B so as to let this reflected light function as another scanning light to scan the object 16 at an angle of incidence difference from that of the scanning light from the mirror 12A, the longitudinal axis of said mirror 15 being arranged to be parallel to the rotating shaft of the roller 17 and located at such a position as allows the scanning light spot from the mirror 15 to be overlapped on the surface of the object with the one from the mirror 12A. Numeral 18 represents a light detecting means for receiving the light coming from the mirror 12A and being reflected by the surface of the object 16. Numeral 19 denotes another light detecting means for receiving the light coming from the other mirror 15 and being reflected by the surface of the object 16.

Figure 7:
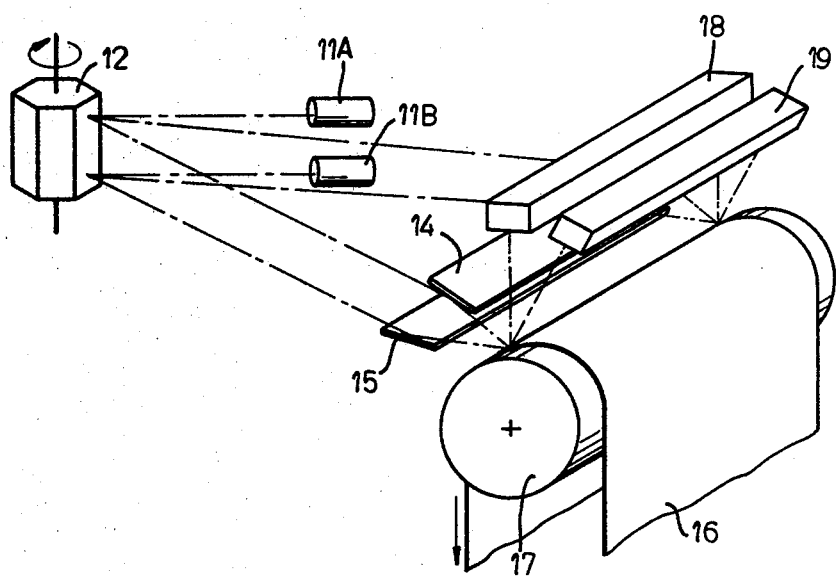
FIG. 7 is a view similar to FIG. 4 showing a third embodiment of the invention.

In FIG. 7, numerals 11A and 11B represent a light beam generating means such as laser oscillators which are arranged to radiate two light beams perpendicular to the rotating shaft of a polygonal rotating mirror 12. The rotating mirror 12 is intended to direct the light beams from the light beam generating means 11A and 11B to the object 16 to be inspected and the rotating shaft of the mirror 12 is arranged to be perpendicular to the rotating shaft of the roller 17 which supports the object 16. Numeral 14 represents a mirror for reflecting the light beam so as to let the reflected light beam from means 11A function as a scanning light beam to scan the surface of the object 16. The longitudinal axis of said mirror 14 is arranged to be parallel to the rotating shaft of the roller 17. The light beam generating means 11A and the rotating mirror 12 are arranged on a common plane, and a plane including the light beam radiated by the light beam generating means 11A and the light reflected by the mirror 12 is arranged to be vertical to the face of the rotating mirror 12. Numeral 15 denotes another mirror for reflecting the light reflected by the rotating mirror 12 so as to let this reflected light function as another scanning light to scan the object 16 at an angle of incidence different from that of the scanning light from the mirror 14, the longitudinal axis of said mirror 15 being arranged to be parallel to the rotating shaft of the roller 17 and located at such a position as allows the scanning light spot from the mirror 15 to be overlapped on the surface of the object with the one from the mirror 14. Numeral 18 represents a light detecting means for receiving the light coming from the mirror 14 and being reflected by the surface of the object 16. Numeral 19 denotes another light detecting means for receiving the light coming from the other mirror 15 and being reflected by the surface of the object 16.

What is claimed is:

1. A scanning inspection apparatus comprising:
   a means for supporting and moving an object to be scanned;
   a light beam generating means including a laser oscillator;
   a rotating mirror for directing a light beam radiated by said light beam generating means to the object;
   a semitransparent mirror for dividing a light beam reflected by the rotating mirror into two light beams;
   plural mirrors for reflecting each of said two light beams divided by the semitransparent mirror, said plural mirrors being so arranged that the light path length of one light beam from the semitransparent mirror to the object is the same as that of the other light beam from the semitransparent mirror to the object and the divided two light beams impinge on a point on the object, each of the light beams having a different angle of incidence with respect to the said point on the surface of the object, with the angle of incidence of one of the light beams being larger than 70° and the angle of incidence of the other light beam being smaller than 45°; and
   light detecting means for receiving the light beams reflected by the surface of the object; wherein a plane including a light path of the light beam radiated by the light beam generating means and a light path of the light beam reflected by the rotating mirror is arranged to be perpendicular to the reflecting face of the rotating mirror.

2. A scanning inspection apparatus according to claim 1 wherein said light detecting means provide pulses and further including a reference pulse generating means for generating a reference pulse signal relating to a point at which the light beams scan on the surface of the object and a means for comparing said reference pulse with the pulses from said light detecting means.

3. A scanning inspection apparatus according to claim 1 wherein the said angle larger than 70° is about 75° and the said angle smaller than 45° is about 30°.

4. A scanning inspection apparatus comprising:
   a means for supporting and moving an object to be scanned;
   two light beam generating means, each including a laser oscillator;
   two rotating mirrors for directing two light beams radiated by said two light generating means to the object;
   at least one mirror for reflecting one of said light beams from said rotating mirror, said one mirror being so arranged that said one mirror reflects said light beam in a direction so that said two light beams impinge on a point on the object through light paths having a length substantially the same as each other, each of the light beams having a different angle of incidence with respect to the said point on the surface of the object, with the angle of incidence of one of the light beams being larger than 70° and the angle of incidence of the other light beam being smaller than 45°; and
   light detecting means for receiving the light beams reflected by the surface of the object; wherein a plane including the light path of a light beam radiated by a light beam generating means and the light path of the light beam reflected by the corresponding rotating mirror is so arranged as to be perpendicular to the reflecting face of the corresponding mirror.

5. A scanning inspection apparatus according to claim 4 wherein said two rotating mirrors, are embodied in a single member.

6. A scanning inspection apparatus according to claim 4 wherein the said angle larger than 70° is about 75° and the said angle smaller than 45° is about 30°.

7. A scanning inspection apparatus according to claim 4 wherein said light detecting means provide pulses and further including a reference pulse generating means for generating a reference pulse signal relating to a point at which the light beams scan on the surface of the object and a means for comparing said reference pulse with the pulses from said light detecting means.

8. A scanning inspection apparatus comprising:
   means for supporting and moving an object to be scanned;
   means, including light beam generating means including a laser oscillator and rotating mirror means, for providing and for directing two light beams to a common point on the surface of said object;
   the paths of said two light beams being of substantially the same length as each other, the path of a light beam radiated by the light beam generating means and the light path of the corresponding light beam reflected by said rotating mirror means lying in a common plane which is perpendicular to a reflecting face of said rotating mirror means, each light beam having a different angle of incidence to the surface of said object, with the angle of incidence of one of the light beams being larger than 70° and the angle of incidence of the other light beam being smaller than 45°;

and light detecting means for receiving the light beams reflected by the surface of said object.

9. A scanning inspection apparatus according to claim 8 wherein the said angle larger than 70° is about 75° and the said angle smaller than 45° is about 30°.

10. A scanning inspection apparatus according to claim 8 wherein said light detecting means provide pulses and further including a reference pulse generating means for generating a reference pulse signal relating to a point at which the light beams scan on the surface of the object and a means for comparing said reference pulse with the pulses from said light detecting means.